United States Patent
Ojima et al.

(10) Patent No.: US 10,928,363 B2
(45) Date of Patent: Feb. 23, 2021

(54) METHOD AND DEVICE FOR CHROMATOGRAPHIC MASS SPECTROMETRY

(71) Applicants: SHIMADZU CORPORATION, Kyoto (JP); NATIONAL UNIVERSITY CORPORATION KOBE UNIVERSITY, Kobe (JP)

(72) Inventors: Noriyuki Ojima, Kyoto (JP); Shuichi Kawana, Kyoto (JP); Yumi Unno, Kyoto (JP); Takero Sakai, Kyoto (JP); Kenichi Obayashi, Kyoto (JP); Yukihiko Kudo, Kyoto (JP); Katsuyuki Taneda, Kyoto (JP); Masaru Yoshida, Kobe (JP); Shin Nishiumi, Kobe (JP); Takashi Kobayashi, Kobe (JP); Takeshi Azuma, Kobe (JP)

(73) Assignees: SHIMADZU CORPORATION, Kyoto (JP); NATIONAL UNIVERSITY CORPORATION KOBE UNIVERSITY, Kobe (JP)

( * ) Notice: Subject to any disclaimer, the term of this patent is extended or adjusted under 35 U.S.C. 154(b) by 117 days.

(21) Appl. No.: 15/885,902

(22) Filed: Feb. 1, 2018

(65) Prior Publication Data
US 2018/0284075 A1    Oct. 4, 2018

(30) Foreign Application Priority Data
Mar. 30, 2017   (JP) .............................. JP2017-069355

(51) Int. Cl.
*G01N 30/06*    (2006.01)
*G01N 30/72*    (2006.01)
(Continued)

(52) U.S. Cl.
CPC ............. *G01N 30/06* (2013.01); *G01N 1/405* (2013.01); *G01N 30/72* (2013.01);
(Continued)

(58) Field of Classification Search
CPC .... G01N 30/06; G01N 30/7206; G01N 30/72; G01N 1/405; G01N 33/487;
(Continued)

(56) References Cited

U.S. PATENT DOCUMENTS

2005/0261838 A1* 11/2005 Andreev ............ G01N 30/8603
 702/22
2012/0252052 A1* 10/2012 Matsukawa ........... C07C 211/48
 435/29

(Continued)

FOREIGN PATENT DOCUMENTS

| JP | 2013246080 A | 12/2013 |
| JP | 2016-510414 A | 4/2016 |
| WO | 2014/125443 A1 | 8/2014 |

OTHER PUBLICATIONS

Aybar, Juan, Quimby, Bruce, Rothweiler, Berhnhard. Use of hydrogen for in situ conditioning of mass spectrometer systems. Poster No. I.06. Agilent Technologies. 2014. (Year: 2014).*

(Continued)

*Primary Examiner* — Jennifer Wecker
*Assistant Examiner* — Michael Paul Shimek
(74) *Attorney, Agent, or Firm* — Sughrue Mion, PLLC (57) ABSTRACT

At least one stable isotope reagent is added to each biological sample and standard sample to prepare biological samples for analysis and standard sample for analysis. The quality of the biological samples is evaluated using data of one set of biological samples for analysis composed of a plurality of biological samples for analysis. Besides, the quality of a pretreatment and/or analysis of each set of (Continued)

samples for analysis is evaluated using data obtained by analyzing the standard sample for analysis before and after an analysis of one set of samples for analysis. An abnormality in a chromatograph or mass analyzer used for the analysis of one set of samples is evaluated by the data obtained by analyzing a sample for device evaluation before and after the analysis of one set of samples for analysis. Thus, the quality of data obtained by chromatographic mass spectrometry on biological samples is comprehensively evaluated.

12 Claims, 6 Drawing Sheets

(51) Int. Cl.
| | | |
|---|---|---|
| *G01N 33/487* | (2006.01) | |
| *G01N 1/40* | (2006.01) | |
| *G01N 30/86* | (2006.01) | |
| *H01J 49/00* | (2006.01) | |
| *G01N 30/88* | (2006.01) | |
| *G01N 1/28* | (2006.01) | |

(52) U.S. Cl.
CPC ..... *G01N 30/7206* (2013.01); *G01N 30/8634* (2013.01); *G01N 33/487* (2013.01); *H01J 49/0027* (2013.01); *H01J 49/0036* (2013.01); *G01N 2001/2893* (2013.01); *G01N 2030/067* (2013.01); *G01N 2030/8813* (2013.01); *G01N 2030/8822* (2013.01); *G01N 2458/15* (2013.01); *G01N 2496/05* (2013.01); *G01N 2560/00* (2013.01)

(58) Field of Classification Search
CPC ....... G01N 30/8634; G01N 2030/8813; G01N 2030/8822; G01N 2001/2893; G01N 2030/067; G01N 2458/15; G01N 2496/05; G01N 2560/00; H01J 49/0027; H01J 49/0036
See application file for complete search history.

(56) References Cited

U.S. PATENT DOCUMENTS

| | | |
|---|---|---|
| 2013/0065320 A1 | 3/2013 | Fedorak et al. |
| 2015/0005183 A1 | 1/2015 | Krizman et al. |
| 2017/0059535 A1* | 3/2017 | Carrard ................ G01N 33/487 |
| 2018/0299448 A1* | 10/2018 | Ojima .................. G01N 33/492 |

OTHER PUBLICATIONS

Nishiumi, Shin et al. "A Novel Serum Metabolomics-Based Diagnostic Approach for Colorectal Cancer." PLoS One (2012) 7 e40459. (Year: 2012).

Dziaman, Tomasz et al. "8-Oxo-7,8-dihydroguanine and uric acid as efficient predictors of survival in colon cancer patients." International Journal of Cancer (2014) 134 376-383. (Year: 2014).

Tan, Binbin et al. "Metabonomics Identifies Serum Metabolite Markers of Colorectal Cancer." Journal of the Proteome (2013) 12 2000-2009 (Year: 2013).

Siminska, Edyta et al. "Amino acid profiling as a method of discovering biomarkers for early diagnosis of cancer." Amino Acids (2016) 48 1339-1345 (Year: 2016).

Chen, Kai-Yuan et al. "A Metabolic Signature of Colon Cancer Initiating Cells." IEEE (2014) 4759-4762. (Year: 2014).

Chuang et al.; "A method for lactate and pyruvate determination in filter paper dried blood spots." Journal of Chromatography A (2009) 1216 8947-8952.

* cited by examiner

| Group | Number of Specimens | Breakdown | Number of QCs |
|---|---|---|---|
| Stage 0 | 190 | 95 Patients; 95 Healthy Individuals | 19 |
| Stage 1 | 269 | 135 Patients; 134 Healthy Individuals | 27 |
| Stage 2 | 270 | 135 Patients; 135 Healthy Individuals | 27 |
| Total | 729 | 270 Patients; 269 Healthy Individuals | 73 |

| Group | Number of Specimens | Breakdown | Number of QCs |
|---|---|---|---|
| Stage 0 | 153/190 | 74/95 Patients; 79/95 Healthy Individuals | 17 |
| Stage 1 | 261/269 | 133/135 Patients; 128/134 Healthy Individuals | 27 |
| Stage 1 | 242/270 | 122/135 Patients; 120/135 Healthy Individuals | 25 |
| Total | 656/729 | 329/365 Patients; 327/364 Healthy Individuals | 69 |

Fig. 8A

| ID | Orig. ID | In vivo metabolite | Data 1 | Data 2 | Data 3 | Data 4 | Data 5 | Data 6 | Data 7 | Data 8 | Data 9 | Data 10 |
|---|---|---|---|---|---|---|---|---|---|---|---|---|
| 1 | 2 | Pyruvic acid-meto-TMS | 0.718809 | 0.444175 | 0.159627 | 0.384229 | 0.484908 | 0.500723 | 0.381357 | 0.049134 | 0.463661 | 0.310961 |
| 2 | 4 | Lactic acid-2TMS(SI ratio) | 0.24136 | 0.220136 | 0.149153 | 0.171189 | 0.273456 | 0.285932 | 0.17818 | 0.146953 | 0.199819 | 0.128947 |
| 3 | 5 | Glycolic acid-2TMS | 0.154464 | 0.133312 | 0.102614 | 0.112997 | 0.154449 | 0.306077 | 0.152209 | 0.101301 | 0.092684 | 0.094817 |
| 4 | 6 | Alanine-2TMS | 1.281645 | 0.653709 | 0.713263 | 0.529224 | 0.99989 | 1.055945 | 1.092501 | 0.973432 | 0.928798 | 0.620081 |
| 5 | 7 | 2-Keto-isovaleric acid-meto-TMS | 0.019341 | 0.012661 | 0.013565 | 0.009532 | 0.010325 | 0.017243 | 0.007016 | 0.013296 | 0.018347 | 0.015085 |
| 6 | 9 | Glycine-2TMS | 0.050396 | 0.062118 | 0.049199 | 0.071917 | 0.070179 | 0.039072 | 0.07047 | 0.057397 | 0.040966 | 0.045222 |
| 7 | 10 | 2-Hydroxybutyric acid-2TMS(SI ratio) | 0.230182 | 1.236529 | 0.694319 | 1.012354 | 0.260101 | 1.511201 | 0.121759 | 0.564222 | 0.619561 | 0.782136 |
| 8 | 14 | Sarcosine-2TMS | 0.102668 | 0.088948 | 0.101316 | 0.100677 | 0.116259 | 0.100935 | 0.104001 | 0.099214 | 0.097912 | 0.116231 |
| 9 | 16 | 2-Aminoisobutyric acid-2TMS | 0.024704 | 0.02066 | 0.020189 | 0.021065 | 0.026214 | 0.021488 | 0.022268 | 0.021613 | 0.024142 | 0.026811 |
| 10 | 17 | 3-Hydroxybutyric acid-2TMS | 0.611635 | 12.3923 | 6.59129 | 21.02369 | 0.455737 | 8.643427 | 0.395752 | 1.362151 | 1.033935 | 8.222595 |
| 11 | 18 | 2-Aminobutyric acid-2TMS | 0.011878 | 0.035864 | 0.019287 | 0.028086 | 0.014589 | 0.043264 | 0.007952 | 0.029569 | 0.020498 | 0.023119 |
| 12 | 25 | 3-Hydroxyisovaleric acid-2TMS | 0.120251 | 0.098782 | 0.100119 | 0.085928 | 0.072271 | 0.102448 | 0.068103 | 0.111446 | 0.177651 | 0.102302 |
| 13 | 26 | Valine-2TMS(SI ratio) | 4.473131 | 2.632533 | 3.146709 | 1.758914 | 2.607605 | 2.582795 | 2.56086 | 3.28984 | 3.533783 | 2.850043 |
| 14 | 30 | Urea-2TMS | 26.26178 | 26.64601 | 23.25921 | 21.49614 | 28.19304 | 20.93308 | 21.15084 | 20.89613 | 24.31956 | 35.2497 |
| 15 | 33 | Serine-2TMS | 0.032315 | 0.04129 | 0.031847 | 0.038517 | 0.044597 | 0.048023 | 0.07409 | 0.038186 | 0.030307 | 0.032909 |
| 16 | 36 | Leucine-2TMS | 4.622463 | 5.029405 | 5.354999 | 3.819754 | 4.931186 | 3.508202 | 2.786994 | 6.715331 | 6.480664 | 6.425288 |
| 17 | 37 | Octanoic acid-TMS | 0.244839 | 0.13376 | 0.172408 | 0.165525 | 0.175049 | 0.15896 | 0.17422 | 0.141842 | 0.169504 | 0.20479 |
| 18 | 38 | Phosphoric acid-3TMS | 6.490315 | 4.389914 | 5.86804 | 6.08935 | 6.878237 | 5.795861 | 6.534842 | 5.470738 | 6.496364 | 7.424555 |
| 19 | 40 | Isoleucine-2TMS(SI ratio) | 1.182001 | 1.11082 | 0.966862 | 0.815389 | 1.130367 | 1.03535 | 0.929848 | 1.232849 | 1.353816 | 1.233448 |
| 20 | 41 | Proline-2TMS | 11.5477 | 4.555819 | 3.542317 | 4.55495 | 5.499791 | 2.487724 | 2.843966 | 5.948026 | 5.669091 | 4.716012 |
| 21 | 45 | Glyceric acid-3TMS | 0.118163 | 0.152587 | 0.105739 | 0.119731 | 0.157473 | 0.150881 | 0.179086 | 0.120024 | 0.101259 | 0.121558 |
| 22 | 50 | Fumaric acid-2TMS(SI ratio) | 0.022102 | 0.012312 | 0.009787 | 0.01501 | 0.012714 | 0.015653 | 0.009245 | 0.008681 | 0.010059 | 0.010432 |
| 23 | 52 | Nonanoic acid-TMS | 0.652244 | 0.44975 | 0.554273 | 0.565205 | 0.591333 | 0.54605 | 0.583582 | 0.536784 | 0.636123 | 0.782937 |
| 24 | 53 | Threonine-3TMS | 0.411698 | 1.003074 | 0.582196 | 0.825707 | 0.732257 | 0.539649 | 0.51846 | 1.179225 | 0.555942 | 0.562849 |
| 25 | 60 | Threitol-4TMS | 0.010982 | 0.005157 | 0.008553 | 0.006272 | 0.006832 | 0.009846 | 0.007873 | 0.002883 | 0.007109 | 0.009752 |
| 26 | 61 | Malic acid-3TMS(SI ratio) | 0.034865 | 0.025727 | 0.028753 | 0.03606 | 0.024646 | 0.055724 | 0.02 | 0.030923 | 0.024656 | 0.041262 |
| 27 | 62 | meso-Erythritol-4TMS | 0.028872 | 0.019824 | 0.013381 | 0.01255 | 0.012938 | 0.026317 | 0.014856 | 0.014391 | 0.019102 | 0.017921 |
| 28 | 66 | 4-Hydroxyproline-3TMS | 0.206946 | 0.330759 | 0.190225 | 0.08894 | 0.092482 | 0.112179 | 0.079662 | 0.135155 | 0.136279 | 0.105849 |
| 29 | 74 | Cysteine-3TMS | 0.105386 | 0.094954 | 0.130897 | 0.063878 | 0.100849 | 0.097796 | 0.043131 | 0.114022 | 0.151877 | 0.123417 |
| 30 | 75 | Creatinine-3TMS | 0.017084 | 0.030939 | 0.014343 | 0.013717 | 0.024775 | 0.017251 | 0.019393 | 0.01469 | 0.029924 | 0.019369 |
| 31 | 78 | 2-Ketoglutaric acid-meto-2TMS | 0.043495 | 0.031482 | 0.038784 | 0.052984 | 0.035717 | 0.068553 | 0.038476 | 0.037351 | 0.041746 | 0.058016 |
| 32 | 83 | Glutamic acid-3TMS(SI ratio) | 0.134104 | 0.097625 | 0.099375 | 0.040411 | 0.093196 | 0.094474 | 0.10452 | 0.130919 | 0.187398 | 0.052835 |

Fig. 8B

| ID | Orig. ID | In vivo metabolite | Data 1 | Data 2 | Data 3 | Data 4 | Data 5 | Data 6 | Data 7 | Data 8 | Data 9 | Data 10 |
|---|---|---|---|---|---|---|---|---|---|---|---|---|
| 33 | 90 | Phenylalanine-2TMS | 1.629277 | 1.116789 | 0.860989 | 0.529948 | 0.907342 | 0.821824 | 0.739807 | 1.184864 | 0.902728 | 1.095313 |
| 34 | 91 | Xylose-meto-4TMS(2) | 0.010235 | 0.005366 | 0.003117 | 0.003286 | 0.002972 | 0.006213 | 0.005005 | 0.004545 | 0.007772 | 0.006491 |
| 35 | 95 | Arabinose-meto-4TMS | 0.033136 | 0.032174 | 0.012734 | 0.020087 | 0.021686 | 0.022199 | 0.033128 | 0.016053 | 0.026936 | 0.02308 |
| 36 | 99 | Ribulose-meto-4TMS | 0.00967 | 0.009742 | 0.008963 | 0.00918 | 0.009247 | 0.010849 | 0.008572 | 0.010161 | 0.006079 | 0.011289 |
| 37 | 100 | Lauric acid-TMS | 0.297272 | 0.071632 | 0.093224 | 0.162767 | 0.04798 | 0.073147 | 0.082801 | 0.056972 | 0.084081 | 0.101469 |
| 38 | 108 | Xylitol-5TMS | 0.021288 | 0.208084 | 0.02221 | 0.01817 | 0.02523 | 0.054178 | 0.31609 | 0.017996 | 0.021817 | 0.030156 |
| 39 | 109 | Arabitol-5TMS | 0.02307 | 0.174608 | 0.015781 | 0.014089 | 0.018192 | 0.047439 | 0.284406 | 0.015312 | 0.016667 | 0.026979 |
| 40 | 130 | Isocitric acid-4TMS | 0.06562 | 0.040711 | 0.03272 | 0.052587 | 0.029186 | 0.103771 | 0.046679 | 0.038563 | 0.03715 | 0.054279 |
| 41 | 131 | 2-Aminopimelic acid-3TMS | 0.856408 | 0.515693 | 0.522229 | 0.895661 | 0.413077 | 0.892687 | 0.620891 | 0.586696 | 0.522287 | 0.850518 |
| 42 | 132 | Citric acid-4TMS(SI ratio) | 0.390981 | 0.230418 | 0.234374 | 0.398849 | 0.186637 | 0.396335 | 0.288734 | 0.257212 | 0.247353 | 0.374921 |
| 43 | 133 | Ornithine-4TMS(SI ratio) | 0.616195 | 0.656825 | 0.404384 | 0.383403 | 0.550554 | 0.656274 | 0.721302 | 0.779893 | 0.462832 | 0.511011 |
| 44 | 141 | 1,5-Anhydro-glucitol-4TMS | 0.073005 | 0.066949 | 0.065043 | 0.028666 | 0.043151 | 0.016618 | 0.049547 | 0.061619 | 0.061549 | 0.074156 |
| 45 | 143 | Sorbose-meto-5TMS(1) | 0.077562 | 0.122621 | 0.08853 | 0.029097 | 0.094045 | 0.046124 | 0.135441 | 0.080137 | 0.023744 | 0.103585 |
| 46 | 146 | Fructose-meto-5TMS(2) | 0.151482 | 0.109578 | 0.066723 | 0.045389 | 0.089884 | 0.066589 | 0.217648 | 0.075986 | 0.072576 | 0.072586 |
| 47 | 151 | 5-Dehydroquinic acid-meto-4TMS | 0.1205 | 0.106612 | 0.123619 | 0.097337 | 0.099424 | 0.155911 | 0.085102 | 0.109942 | 0.113853 | 0.094399 |
| 48 | 152 | Glucose-meto-5TMS(1) | 21.28092 | 17.92226 | 20.58237 | 16.20164 | 17.1913 | 26.79726 | 14.20196 | 17.79374 | 18.68869 | 16.13021 |
| 49 | 153 | Hippuric acid-TMS | 0.208062 | 0.171488 | 0.198038 | 0.157506 | 0.173757 | 0.240606 | 0.137946 | 0.174987 | 0.192601 | 0.16409 |
| 50 | 157 | Galactose-meto-5TMS(2) | 12.48897 | 9.689233 | 11.69056 | 9.261897 | 10.60423 | 14.13392 | 8.814775 | 10.0608 | 12.49485 | 11.31843 |
| 51 | 161 | Glucosamine-5TMS(1) | 0.214296 | 0.166418 | 0.196491 | 0.159501 | 0.172289 | 0.253057 | 0.142543 | 0.177279 | 0.201005 | 0.186283 |
| 52 | 164 | Lysine-4TMS | 0.486149 | 0.782533 | 0.86395 | 0.520709 | 0.715466 | 1.04674 | 0.917522 | 1.640881 | 1.008942 | 0.891784 |
| 53 | 165 | Glucuronic acid-meto-5TMS(1) | 0.059466 | 0.041612 | 0.057052 | 0.037122 | 0.030661 | 0.051746 | 0.049389 | 0.042408 | 0.052811 | 0.047949 |
| 54 | 172 | Ascorbic acid-4TMS | 0.010616 | 0.00819 | 0.00852 | 0.005437 | 0.006399 | 0.01172 | 0.004708 | 0.008042 | 0.008856 | 0.007082 |
| 55 | 174 | Tyrosine-3TMS(SI ratio) | 1.156613 | 0.883181 | 0.85137 | 0.756203 | 0.679587 | 1.011857 | 1.082964 | 1.419806 | 0.979645 | 0.892805 |
| 56 | 183 | Glucaric acid-6TMS | 0.008529 | 0.006316 | 0.010759 | 0.007054 | 0.004425 | 0.007602 | 0.009212 | 0.006356 | 0.005407 | 0.005436 |
| 57 | 186 | Palmitoleic acid-TMS | 0.003832 | 0.014135 | 0.063271 | 0.040871 | 0.006825 | 0.029374 | 0.001679 | 0.01903 | 0.031032 | 0.066649 |
| 58 | 187 | Inositol-6TMS | 0.709776 | 0.892733 | 0.667662 | 0.765336 | 0.692856 | 1.177411 | 0.775474 | 0.550678 | 0.733325 | 1.137305 |
| 59 | 191 | Uric acid-4TMS | 0.996789 | 2.165546 | 1.281754 | 0.461792 | 0.815569 | 1.145054 | 1.202258 | 1.147679 | 2.010159 | 1.778788 |
| 60 | 197 | Kynurenine-3TMS | 0.00844 | 0.00471 | 0.002923 | 0.000919 | 0.003288 | 0.003205 | 0.003031 | 0.004458 | 0.004167 | 0.003493 |
| 61 | 201 | Tryptophan-3TMS(SI ratio) | 0.926584 | 0.946284 | 0.820616 | 0.875418 | 0.87546 | 1.182957 | 0.741077 | 1.27245 | 1.028487 | 1.121251 |
| 62 | 203 | Elaidic acid-TMS | 0.04992 | 0.123618 | 0.187007 | 0.166027 | 0.063046 | 0.156659 | 0.040692 | 0.139826 | 0.157379 | 0.150813 |
| 63 | 212 | Sucrose-8TMS | 0.017517 | 0.011724 | 0.002954 | 0.002999 | 0.056963 | 0.007819 | 0.005572 | 0.003237 | 0.014139 | 0.011688 |
| 64 | 213 | Maltose-meto-8TMS(1) | 0.009985 | 0.004752 | 0.003141 | 0.000828 | 0.002539 | 0.00475 | 0.003178 | 0.002883 | 0.010799 | 0.008092 |

METHOD AND DEVICE FOR CHROMATOGRAPHIC MASS SPECTROMETRY

CROSS REFERENCE TO RELATED APPLICATIONS

This application claims priority from Japanese Patent Application No. 2017-069355, filed on Mar. 30, 2017.

TECHNICAL FIELD

The present invention relates to a method and device for chromatographic mass spectrometry which employs chromatography, such as a gas chromatography or liquid chromatography, combined with mass spectrometry. More specifically, it relates to a method for chromatographic mass spectrometry and chromatograph mass spectrometer suitable for collecting data to be used for a difference analysis for investigating differences among data on biological samples (e.g. blood, urine, or saliva) collected from a plurality of groups of subjects, such as the healthy individuals and cancer patients.

BACKGROUND ART

Chromatographic mass spectrometry, which employs gas chromatography, liquid chromatography or other types of chromatography combined with mass spectrometry, has been widely used in various areas, such as the medical care, drugs, foods and environment. There are various techniques for analyzing data obtained by chromatographic mass spectrometry. One of those techniques is the difference analysis for investigating differences among two or more groups of data. A specific example of the difference analysis is an analyzing process in which a peak that is not present in chromatograms and mass spectra of biological samples collected from healthy individuals but is present in chromatograms and mass spectra of biological samples collected from cancer patients is searched for in order to detect a specific protein that is only found in cancer patients and not in healthy individuals (i.e. a biomarker for the cancerous disease concerned).

For example, the search for a biomarker using a chromatograph mass spectrometer is performed as follows: One or more proteins contained in a biological sample collected from a subject (healthy individual or patient) are degraded into a plurality of peptides by a digestive enzyme to obtain a peptide mixture. The peptide mixture is subsequently introduced into a liquid chromatograph to separate those peptides according to their respective retention times. The sample containing those peptides which have been separated according to their retention times is subjected to a measurement with a mass spectrometer to collect data which reflect the signal intensities of the ions originating from the peptides.

A peak originating from one peptide appears at the retention time (RT) corresponding to that peptide as well as at a mass-to-charge ratio m/z corresponding to that peptide. In other words, the position at which a peak originating from one peptide appears can be expressed by the coordinates (RT, m/z) or a two-dimensional vector including those values as its elements. Accordingly, whether or not the peptide is present in a group of healthy individuals or cancer patients can be determined by checking whether or not a peak is present at (RT, m/z) corresponding to that peptide.

Biological samples used in the search for a biomarker are collected from subjects in hospitals, clinics or other medical institutions. It is impractical to require all institutions to collect samples and perform measurements by the same procedure, under the same conditions and with the same quality. Furthermore, in some cases, biological samples collected from subjects in a medical institution are stored for a certain period of time and collectively subjected to a measurement at a later point in time when a certain number of samples have been collected. In such a case, the storage temperature and storage time will vary from one biological sample to another. Due to such variations in the procedure, conditions and quality of the collection and measurement as well as the storage temperature, storage time and other factors, a peak originating from the same substance may exhibit a displacement in retention time or a change in the signal intensity at a certain mass-to-charge ratio. Such a displacement or change may be incorrectly judged as a difference between healthy individuals and patients.

In regard to this problem, for example, Patent Literature 1 discloses a method in which a substance that is susceptible to the analyzing conditions, storage time, storage temperature and other factors is selected from the components contained in biological samples used for an analysis of in vivo metabolism and used as an index for evaluating the quality of biological samples.

CITATION LIST

Patent Literature

Patent Literature 1: JP 2016-510414 A

SUMMARY OF INVENTION

Technical Problem

By adopting the method described in Patent Literature 1, measurement data of a biological sample which has been judged to be low in quality can be excluded from the data to be used for the difference analysis. A difference which occurs due to some irrelevant causes, such as a variation in the analyzing conditions, storage time, storage temperature or other factors, can thereby be prevented from being incorrectly judged to be a difference observed between healthy individuals and patients.

However, in addition to the aforementioned factors, there are other factors which can affect the data obtained by performing chromatographic mass spectrometry on biological samples (i.e. retention time and mass-to-charge ratio), such as the performance of the instruments or devices used for collecting biological samples, that of the apparatus used for the chromatographic mass spectrometry of biological samples, as well as the malfunctioning of the apparatus. The influence of such factors is not considered in the method of Patent Literature 1.

Furthermore, biological samples have significant individual differences due to various factors, such as the age, gender and race of the subject, as well as genetic factors. Accordingly, biological samples in the same group may exhibit small fluctuations in their data depending on the components contained in each sample. If data of a sample or samples in a group has substantially exceeded the range of fluctuations attributable to the individual differences (subjects), it is necessary to remove that data from the group to prevent the boundaries between the groups from being affected by the fluctuations. With the method described in Patent Literature 1, it is difficult to distinguish between the fluctuations due to the individual differences of the biological samples and the variations due to other factors.

The problem to be solved by the present invention is enable comprehensive evaluation of the quality of the data obtained by performing chromatographic mass spectrometry on biological samples.

Solution to Problem

The first mode of the method for chromatographic mass spectrometry according to the present invention developed for solving the previously described problem is a method including the steps of temporally separating components in a sample by a chromatograph, and subsequently separating and detecting ions originating from the components according to the mass-to-charge ratios of the ions by a mass analyzer, the method further including:

a) a first preparation process in which a plurality of biological samples for analysis are prepared by adding, to each of a plurality of original biological samples, at least one stable isotope reagent obtained by stable isotopically labeling a predetermined in vivo metabolite contained in the original biological samples, and then performing a predetermined pretreatment for chromatographic mass spectrometry on the original biological samples;

b) a second preparation process in which a standard sample for analysis is prepared by adding, to an original standard sample, the same stable isotope reagent as the one added to the biological samples for analysis, and then performing, on the original standard sample, the same pretreatment as the one performed on the original biological samples;

c) a first analyzing process in which the plurality of biological samples for analysis are collectively analyzed as one set;

d) a second analyzing process in which the standard sample for analysis is analyzed before and after the first analyzing process;

e) a first evaluation process in which: a peak intensity corresponding to the stable isotope reagent contained in each of the biological samples for analysis is determined from each of the mass spectra created based on data obtained in each of the first analyzing process; a median or average of the peak intensity corresponding to the at least one stable isotope reagent contained in the plurality of biological samples for analysis is calculated; and the quality of each of the original biological samples and the first preparation process are evaluated based on whether or not the peak intensity corresponding to the stable isotope reagent contained in each of the biological samples for analysis is within a predetermined range centering on the median or average; and f) a second evaluation process in which the quality of the pretreatment and/or the quality of the analysis is evaluated by mass spectra created based on the data obtained in the second analyzing process.

The second mode of the method for chromatographic mass spectrometry according to the present invention developed for solving the previously described problem is a method including the steps of temporally separating components in a sample by a chromatograph, and subsequently separating and detecting ions originating from the components according to the mass-to-charge ratios of the ions by a mass analyzer, the method further including:

a) a first preparation process in which a plurality of biological samples for analysis are prepared by adding, to each of a plurality of original biological samples, at least one stable isotope reagent obtained by stable isotopically labeling a predetermined in vivo metabolite contained in the original biological samples, and then performing a predetermined pretreatment for chromatographic mass spectrometry on the original biological samples;

b) a second preparation process in which a standard sample for analysis is prepared by adding, to an original standard sample, the same stable isotope reagent as the one added to the biological samples for analysis, and then performing, on the original standard sample, the same pretreatment as the one performed on the original biological samples;

c) a first analyzing process in which the plurality of biological samples for analysis are collectively analyzed as one set;

d) a second analyzing process in which the standard sample for analysis is analyzed before and after the first analyzing process;

e) a first evaluation process in which the quality of each of the original biological samples is evaluated based on whether or not a peak of an ion corresponding to the stable isotope reagent contained in each of the biological samples for analysis is present on a mass spectrum created based on data obtained in each of the first analyzing process; and f) a second evaluation process in which the quality of the pretreatment and/or the quality of the analysis is evaluated by mass spectra created based on the data obtained in the second analyzing process.

For example, the chromatograph in the present invention is a gas chromatograph or liquid chromatograph.

The mass analyzer may be a commonly known single-type mass analyzer. Other types of mass analyzers may also be used, such as a triple quadrupole mass analyzer, Q-TOF mass analyzer, TOF-TOF mass analyzer, ion trap mass analyzer, or ion trap time-of-flight mass analyzer. The use of a triple quadrupole mass analyzer, Q-TOF mass analyzer, TOF-TOF mass analyzer, ion trap mass analyzer, ion trap time-of-flight mass analyzer, or similar mass analyzer enables a high-sensitivity analysis even for a sample which contains a considerable amount of foreign substances other than the substances to be analyzed. Such a device improves the stability of the analysis, and therefore, is suitable for the method for chromatographic mass spectrometry according to the present invention.

The "standard sample" is a sample which contains a plurality of kinds of components contained in biological samples, with their contents adjusted at their respective normal values. In the case where the biological samples are plasma or serum, a commercially available standard sample can be used.

The "stable isotope reagent" in the method for mass spectrometry according to the present invention is a reagent obtained from a substance known as an in vivo metabolite contained in biological samples, by replacing some of the atoms constituting the substance with their stable isotope elements. Examples of the stable isotope reagents are: $^{13}C_3$-lactic acid, $^{13}C_2$-oxalic acid, $^{2}H_3$-sarcosine, $^{2}H_8$-valine, $^{13}C_3$-dihydroxyacetone, $^{2}H_{10}$-isoleucine, $^{13}C_4$-fumaric acid, $^{13}C_4$-malic acid, $^{2}H_3$-aspartic acid, $^{13}C_5$-glutamic acid, $^{13}C_6$-4-hydroxybenzoic acid, $^{2}H_3$-lauric acid, $^{13}C_5$-ribose, $^{13}C_2$-taurine, $^{2}H_4$-citric acid, $^{2}H_7$-ornithine, $^{13}C_6$-tyrosine, $^{13}C_6$-dopa, $^{2}H_6$-kynurenine, $^{2}H_8$-cystamine, $^{13}C_{11}$-tryptophan, and $^{2}H_3$-2-hydroxybutyric acid. The number of kinds of stable isotope reagents to be added to biological samples may be one or more. The number and kinds of stable isotope reagents to be added should be determined according to the kind of biological samples to be analyzed as well as the number and kinds of in vivo metabolites to be analyzed among all in vivo metabolites contained in those biological samples. The contents of in vivo metabolites easily change due to many factors, such as the various processes performed when biological samples are collected from subjects (e.g. the mixing of anticoagulant, centrifugal separation, cold storage, and other operations in the case of collecting serum or plasma as the biological samples), as well as the difference in the conditions, procedure and other aspects of the pretreatment for chromatographic mass spectrometry (e.g. deproteinization and oximation). In the present invention, a plurality of biological samples for analysis to which at least one such stable isotope reagent is added are prepared, and those biological samples for analysis are collectively analyzed as one set. To "collectively analyze" includes both the case where the plurality of biological samples for analysis are analyzed in parallel and the case where those samples are analyzed in series. One set of biological samples for analysis may be composed of a plurality of biological samples collected from subjects belonging to the same group, or it may be composed of a plurality of biological samples collected from subjects belonging to different groups.

Furthermore, in the method for mass spectrometry according to the present invention, a standard sample for analysis to which the same stable isotope reagent as the one added to the biological samples for analysis, is analyzed before the collective analysis of one set of biological samples for analysis as well as after the collective analysis. That is to say, a series of processes including an analysis of the standard sample for analysis, an analysis of one set of biological samples, and an analysis of the standard sample for analysis, are successively performed in the present invention. If there are two or more sets of biological samples for analysis and those sets of biological samples for analysis should be analyzed in series, the analysis of the standard sample for analysis may be performed only one time between the analysis of one set of biological samples and the analysis of the next set of biological samples. In this case, the analysis of the standard sample for analysis corresponds to both the "subsequent analysis" for the analysis of one set of biological samples and the "previous analysis" for the next set of biological samples. Otherwise, when there are two or more sets of biological samples for analysis and those sets of biological samples for analysis should be analyzed in series, the analysis of the standard sample for analysis may be performed one time before the analysis of the first set of biological samples and one time after the analysis of the last set of biological samples. In this case, the analysis of the standard sample for analysis performed before the analysis of the first set of biological samples corresponds to the "previous analysis" for the analysis of all sets of biological samples, while the one performed after the analysis of the last set of biological samples corresponds to the "subsequent analysis" for the analysis of all sets of biological samples.

In the first mode of the method for chromatographic mass spectrometry according to the present invention, a mass spectrum is created based on each of the sets of data obtained by collectively analyzing the standard sample for analysis and the one set of biological samples for analysis. Then, the peak intensity corresponding to the standard sample for analysis and the peak intensity corresponding to the stable isotope reagent contained in each biological sample for analysis are determined from the mass spectrum. Since biological samples have significant individual differences, the data obtained by the analysis of those samples exhibit a specific range of fluctuations even when those samples are collected from subjects belonging to the same group. Accordingly, in the first mode of the present invention, the peak intensity corresponding to the stable isotope reagent determined from each of the sets of data obtained for one set of biological samples for analysis is tested in the first evaluation process to determine whether or not its value is within a predetermine range centering on the median or average of the peak intensities corresponding to the stable isotope reagent in the one set of biological samples for analysis. If the value is outside the predetermine range, a judgment is given that there is a problem, such as a problem with the biological sample itself or with the processes or pretreatment performed on that biological sample, which may cause a considerable change that exceeds the range of fluctuations attributable to the individual differences (i.e. the quality of the biological sample and/or that of the first preparation process is low).

If a problem exists in the original biological sample in the first place, a peak which should appear on the mass spectrum of the biological sample for analysis corresponding to the biological sample in question (i.e. the peak of an ion corresponding to the stable isotope reagent contained in the biological sample for analysis) will not appear. Accordingly, in the second mode of the present invention, a mass spectrum of each of the plurality of biological samples for analysis is created in the first evaluation process, based on each set of data obtained by collectively analyzing the biological samples for analysis, and the quality of each original biological sample is evaluated based on whether or not the peak of an ion corresponding to the stable isotope reagent contained in the biological samples for analysis is present on the mass spectrum.

In both the first and second modes of the method for mass spectrometry according to the present invention, an internal standard reagent which is not contained in a living organism may be contained in each of the biological samples for analysis.

If this configuration is applied in the first mode of the present invention, the peak intensity corresponding to the stable isotope reagent determined from each of the sets of data obtained for one set of biological samples for analysis is tested in the first evaluation process to determine whether or not its value is within a predetermine range centering on the median or average of the peak intensities corresponding to the internal standard reagent or stable isotope reagent in the one set of biological samples for analysis. If the value is outside the predetermine range, a judgment is given that there is a problem, such as a problem with the biological sample itself or with the processes or pretreatment performed on that biological sample, which may cause a considerable change that exceeds the range of fluctuations attributable to the individual differences (i.e. the quality of the biological sample and/or that of the first preparation process is low). In the case of the second mode of the present invention, a mass spectrum of each of the plurality of biological samples for analysis is created in the first evaluation process, based on each set of data obtained by collectively analyzing the biological samples for analysis, and the quality of each original biological sample is evaluated based on whether or not the peak of an ion corresponding to the internal standard reagent or stable isotope reagent contained in the biological samples for analysis is present on the mass spectrum.

In any of the first and second modes of the method for mass spectrometry according to the present invention, in the second evaluation process, the quality of the pretreatment and/or the quality of the analysis is evaluated based on mass spectra created based on the data obtained by analyzing the standard sample for analysis before and after the analysis of one set of biological samples for analysis.

The method for mass spectrometry according to the present invention may further include: a third analyzing process in which a sample for device evaluation is analyzed before and after the first analyzing process; and a third evaluation process in which an abnormality in a chromatograph or a mass analyzer used for the analysis is evaluated by a mass chromatogram or a mass spectrum created based on data obtained in the third analyzing process. Since the biological samples for analysis are subjected to the same pretreatment as the standard sample for analysis, it is possible to presume that the data of the one set of biological samples should have a problem if the pretreatment has been evaluated as being low in quality or if the chromatograph or mass analyzer has been evaluated as having an abnormality.

In the method for mass spectrometry according to the present invention, $^{13}C_6$-4-hydroxybenzoic acid may preferably be added as the stable isotope reagent to the biological samples for analysis and the standard sample for analysis. $^{13}C_6$-4-hydroxybenzoic acid is hardly affected by the condition of the biological samples. Therefore, an abnormality in the pretreatment can be evaluated with high sensitivity based on the peak intensity corresponding to the stable isotope reagent.

Furthermore, if a comparison of the two mass spectra created based on the data of the standard sample for analysis analyzed before and after the analysis of one set of biological samples for analysis has revealed that a difference equal to or larger than a predetermined amount exists between the two mass spectra, it is possible to give the evaluation that there is a problem with the procedure, condition and/or quality of the pretreatment.

Furthermore, an abnormality in the chromatograph or mass analyzer can be evaluated by comparing mass chromatograms or mass spectra created based on the data obtained by analyzing the sample for device evaluation before and after an analysis of one set of biological samples for analysis. As the sample for device evaluation, a solution of a plurality of kinds of normal alkanes selected from the normal alkanes with carbon numbers ranging from 7 to 33, or a solution containing an octafluoronaphthalene, may be adopted. An abnormality in the column of the chromatograph can be evaluated by using the former solution, while an abnormality in the mass analyzer can be evaluated by using the latter solution.

Chromatograph mass spectrometers are also included within the scope of the present invention.

The first mode of the mass spectrometer according to the present invention is a chromatograph mass spectrometer in which a chromatograph for temporally separating components in a sample is coupled with a mass analyzer for generating ions from the components temporally separated by the chromatograph and for separating and detecting the ions according to the mass-to-charge ratios of the ions, the chromatograph mass spectrometer including:

a) a method file storage section for storing an analysis method file including: a description of a procedure for collectively analyzing a plurality of biological samples for analysis as one set, the plurality of biological samples for analysis prepared by adding, to each of a plurality of original biological samples, at least one stable isotope reagent obtained by stable isotopically labeling a predetermined in vivo metabolite contained in the original biological samples, and then performing a predetermined pretreatment for chromatographic mass spectrometry on the original biological samples; and a procedure for analyzing a standard sample for analysis before and after an analysis of the plurality of biological samples for analysis, the standard sample for analysis prepared by adding, to an original standard sample, the same stable isotope reagent as the one added to the biological samples for analysis, and then performing, on the original standard sample, the same pretreatment as the one performed for the biological samples for analysis;

b) an analysis executer for executing an analysis according to the procedures in the analysis method file stored in the method file storage section;

c) a graph creator for creating a mass chromatogram and a mass spectrum based on data obtained with the mass analyzer;

d) a first evaluator for determining, from mass spectra of the standard sample for analysis and the plurality of biological samples for analysis created by the graph creator, a peak intensity corresponding to the stable isotope reagent contained in the standard sample for analysis and a peak intensity corresponding to the stable isotope reagent contained in each of the biological samples for analysis, for calculating a median or average of the peak intensity corresponding to the at least one stable isotope reagent contained in the plurality of biological samples for analysis, and for evaluating the quality of each of the original biological samples and the analysis of the plurality of biological samples for analysis performed by the analysis executer, based on whether or not the peak intensity corresponding to the stable isotope reagent contained in each of the biological samples for analysis is within a predetermined range centering on the median or average; and e) a second evaluator for evaluating the quality of the pretreatment and/or the quality of the analysis, by comparing mass chromatograms or mass spectra of the standard sample for analysis analyzed before and after the analysis of the plurality of biological samples for analysis, where the mass chromatograms or the mass spectra are created by the graph creator.

The second mode of the mass spectrometer according to the present invention is a chromatograph mass spectrometer in which a chromatograph for temporally separating components in a sample is coupled with a mass analyzer for generating ions from the components temporally separated by the chromatograph and for separating and detecting the ions according to the mass-to-charge ratios of the ions, the chromatograph mass spectrometer including:

a) a method file storage section for storing an analysis method file including: a description of a procedure for collectively analyzing a plurality of biological samples for analysis as one set, the plurality of biological samples for analysis prepared by adding, to each of a plurality of original biological samples, at least one stable isotope reagent obtained by stable isotopically labeling a predetermined in vivo metabolite contained in the original biological samples, and then performing a predetermined pretreatment for chromatographic mass spectrometry on the original biological samples; and a procedure for analyzing a standard sample for analysis before and after an analysis of the plurality of biological samples for analysis, the standard sample for analysis prepared by adding, to an original standard sample, the same stable isotope reagent as the one added to the biological samples for analysis, and then performing, on the original standard sample, the same pretreatment as the one performed for the biological samples for analysis;

b) an analysis executer for executing an analysis according to the procedures in the analysis method file stored in the method file storage section;

c) a graph creator for creating a mass chromatogram and a mass spectrum based on data obtained with the mass analyzer;

d) a first evaluator for determining the quality of each of the original biological samples, based on whether or not the peak of an ion corresponding to the stable isotope reagent contained in each of the biological samples for analysis is detected from mass spectra of the plurality of biological samples for analysis created by the graph creator; and e) a second evaluator for evaluating the quality of the pretreatment and/or the quality of the analysis, based on mass chromatograms or mass spectra of the standard sample for analysis analyzed before and after the analysis of the plurality of biological samples for analysis, where the mass chromatograms or the mass spectra are created by the graph creator.

In a preferable form of the first or second mode of the mass spectrometer according to the present invention, the analysis method file includes a description of a procedure for analyzing a sample for device evaluation before and after an analysis of the plurality of biological samples for analysis, and the chromatograph mass spectrometer further includes a third evaluator for evaluating an abnormality in the chromatograph or the mass analyzer used for the analysis, based on a mass chromatogram or a mass spectrum of the sample for device evaluation analyzed before and after the analysis of the plurality of biological samples for analysis, where the mass chromatogram or the mass spectrum is created by the graph creator.

Advantageous Effects of the Invention

As described to this point, in the present invention, at least one stable isotope reagent is added to each of the original biological samples and a standard sample to prepare biological samples for analysis and a standard sample for analysis. The quality of each of the original biological samples is evaluated by using data of one set of biological samples for analysis composed of a plurality of biological samples for analysis, while the quality of the pretreatment and/or analysis of each set of samples for analysis is evaluated using data obtained by analyzing the standard sample for analysis before and after the analysis of the set of samples for analysis. Thus, the quality of the data obtained by performing chromatographic mass spectrometry on the biological samples can be comprehensively evaluated. By additionally analyzing a sample for device evaluation before and after an analysis of the plurality of samples for analysis, an abnormality in a chromatograph or mass analyzer used for the analysis can also be evaluated by a mass chromatogram or mass spectrum created based on the analysis data of the sample for device evaluation, so that the quality of the data obtained by performing chromatographic mass spectrometry on the biological samples can be even more comprehensively evaluated.

BRIEF DESCRIPTION OF DRAWINGS

FIG. 8A is Part 1 of the table showing the area ratios of 64 components contained in each of the specimens evaluated as being high in quality, determined from the data of those specimens.

FIG. 8B is Part 2 of the table showing the area ratios of 64 components contained in each of the specimens evaluated as being high in quality, determined from the data of those specimens.

DESCRIPTION OF EMBODIMENTS

An embodiment of a method and device for gas chromatographic mass spectrometry in which the method and device for chromatographic mass spectrometry according to the present invention is applied is hereinafter described with reference to the attached drawings.

Figure 1:
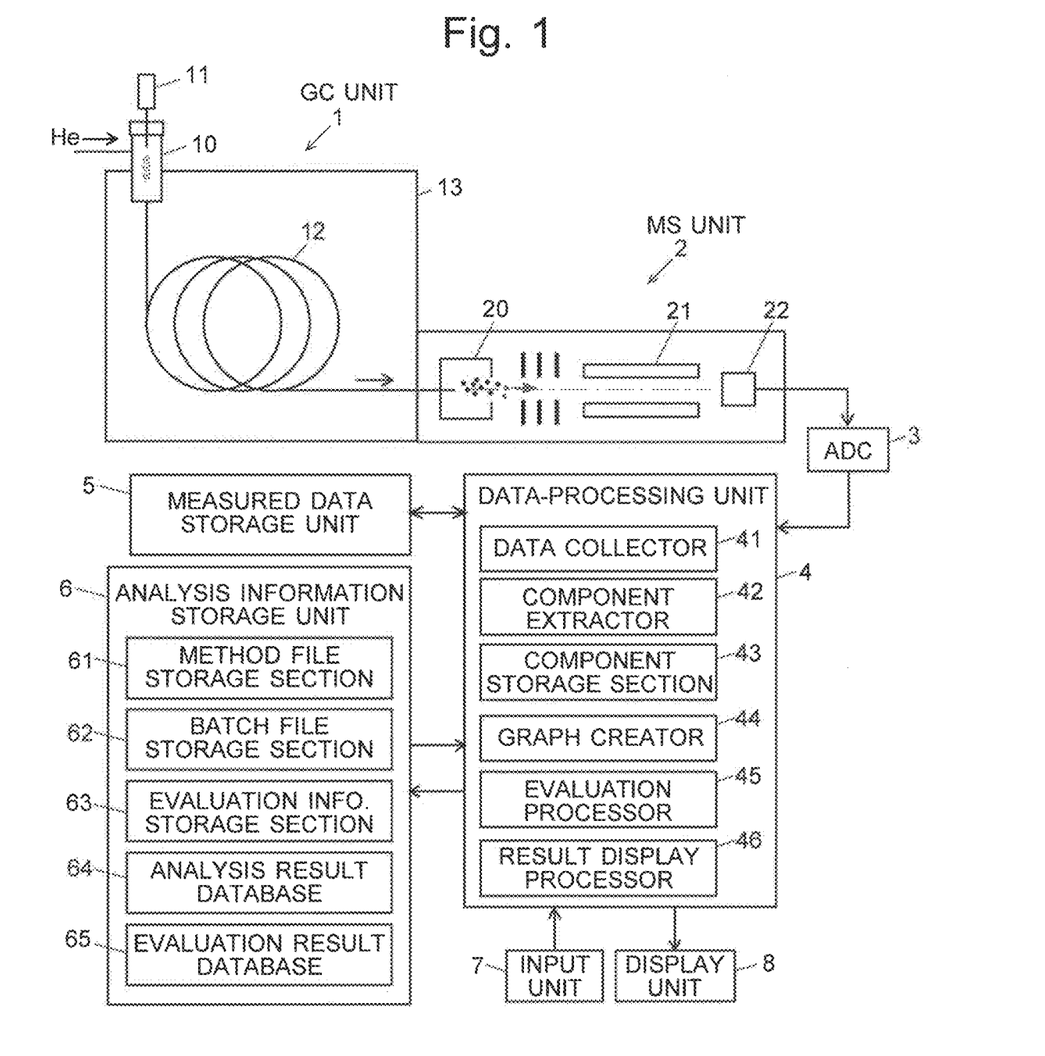
FIG. 1 is a schematic configuration diagram of a gas chromatograph mass spectrometer according to one embodiment of the present invention.

As shown in FIG. 1, the gas chromatograph mass spectrometer (GC-MS) according to the present embodiment includes a GC unit 1 and an MS unit 2. The GC unit 1 includes a sample vaporization chamber 10, injector 11, column 12, and column oven 13 containing the column 12. The MS unit 2 includes an ion source 20, quadrupole mass filter 21, and ion detector 22. Detection signals generated by the ion detector 22 are converted into digital data by an analogue-to-digital converter (ADC) 3 and sent to a data-processing unit 4.

In the GC unit 1, a stream of carrier gas, such as helium, is supplied through the sample vaporization chamber 10 to the column 12 at a constant flow rate. Upon receiving a command from a control unit (not shown), the injector 11 injects a trace amount of sample into the sample vaporization chamber 10 at a predetermined timing. The injected sample is instantly vaporized and carried by the stream of carrier gas into the column 12. While passing through the column 12 whose temperature is controlled by the column oven 13, the various components contained in the sample are separated from each other and exit from the outlet of the column 12 with different amounts of time lag.

The stream of sample gas exiting from the column 12 is introduced into the ion source 20 in the MS unit 2. The component molecules contained in the sample gas are ionized, for example, by electron ionization. The generated ions are introduced into the quadrupole mass filter 21, where only an ion having a specific mass-to-charge ratio m/z corresponding to the voltage applied to the quadrupole mass filter 21 is selectively allowed to pass through the same filter and reach the ion detector 22. A quadrupole driver (not shown) continuously and repeatedly changes the voltage applied to the quadrupole mass filter 21 within a predetermined voltage range to perform a mass scan over a predetermined mass-to-charge-ratio range. Thus, in the MS unit 2, a scan measurement over a predetermined mass-to-charge-ratio range is performed for the sample gas which is sequentially introduced with the passage of time. Through the ADC 3, a stream of data having the dimensions of mass-to-charge ratio, time and signal intensity is sent to the data-processing unit 4.

The data-processing unit 4 includes a data collector 41, component extractor 42, component storage section 43, graph creator 44, evaluation processor 45, result display processor 46 and other sections as its functional blocks. The graph creator 44 creates a mass spectrum and mass chromatogram based on the data having the dimensions of mass-to-charge ratio, time and signal intensity. A measured data storage unit 5, analysis information storage unit 6, input unit 7 and display unit 8 are connected to the data-processing unit 4.

The analysis information storage unit 6 includes a method file storage section 61 for storing method files and a batch file storage section 62 for storing batch files, as well as an evaluation information storage section 63, analysis result database 64, evaluation result database 65, and other sections. The evaluation information storage section 63 holds the following items of information for all target components contained in samples: retention time, standard mass spectrum, characteristic mass-to-charge ratios (e.g. the mass-to-charge ratios of the target ion and qualifier ion), and information used for evaluating the quality of samples or other aspects of the analysis (e.g. the mass-to-charge ratios and/or retention times of relevant ions, such as an ion originating from a stable isotope reagent or a detection ion originating from a reference compound contained in a sample for device evaluation; and the mass peak intensity threshold for evaluating a sample or device itself).

A batch file stored in the batch file storage section 62 is a file in which the ID of a vial containing a sample and the name of the method file to be used for analyzing that sample are described for analyses of a plurality of samples to be performed in series. The batch file may be created by a controller (not shown) with the help of a user who enters, through the input unit 7, the information to written in the batch file, such as the vial ID and the kind of method file. Alternatively, the controller may automatically create the batch file when vials which contain samples to be analyzed are set in the GC-MS and the IDs given to those vials are read. As will be described later, in the GC-MS according to the present embodiment, the analyses of one or two kinds of samples for device evaluation, one standard biological sample and a plurality of biological samples are handled as one batch of analyses, and the analyses of those samples are performed in series. A method file includes: the temperature of the sample vaporization chamber 10, the temperature of the column oven 13, the diameter and length of the column 12, the kind and particle diameter of the stationary phase, and the kind and flow rate of the mobile phase in the GC unit 1 to be used for the analysis; the temperature of the ion source 20, the kind of ion detector 22, and the range of mass-to-charge ratios in the MS unit 2; and other related information.

The data collector 41 collects the data received in the previously described manner along with the execution of the analysis and stores them in the measured data storage unit 5. After the completion of the measurement, upon receiving the command to execute the data evaluation process (the intended quantitative determination process) through the input unit 7, the evaluation processor 45 reads measured data of the sample for device evaluation, standard sample and biological samples from the measured data storage section 5, as well as the information related to the evaluation of the data from the evaluation information storage section 63, and performs a characteristic evaluation process (which will be described later) based on the data obtained in each batch of analyses. The evaluation processor 45 corresponds to the first through third evaluators in the present invention. The result display processor 46 stores the result of the evaluation process in the evaluation result database 65 and displays the evaluation result on the display unit 8. The component extractor 42 determines the quantity of a target component contained in a biological sample, based on the mass chromatogram at the mass-to-charge ratio of the target ion or qualifier ion for that target component. The result display processor 46 displays the result of the quantitative analysis on the display unit 8.

Figure 2:
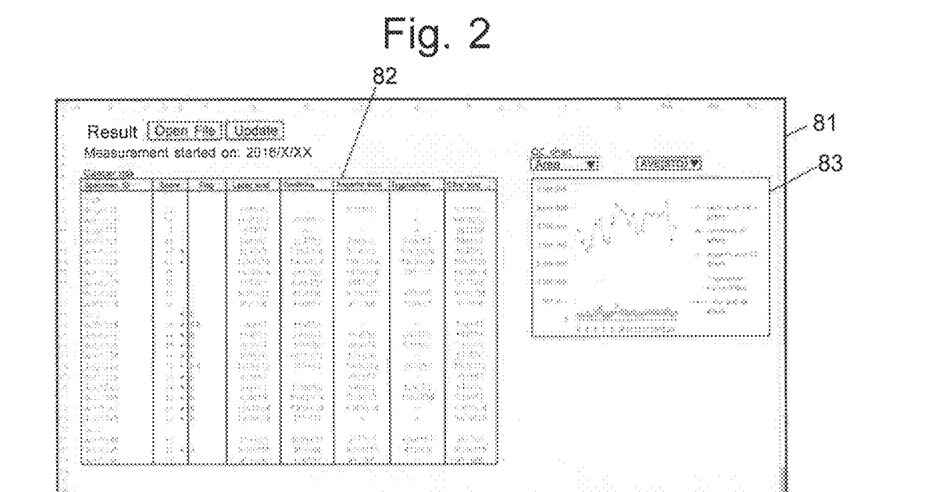
FIG. 2 is a diagram showing one example of the display screen on a display unit.

FIG. 2 shows one example of the display screen of the display unit 8. A table 82 and a graph 83 are displayed on the display screen 81. The table 82 describes the ID of each sample (specimen), evaluation result based on the sample for device evaluation, peak area of the stable isotope reagent, and other data. The graph 83 is created based on the data of each sample.

The data-processing unit 4 and the controller (not shown) are actually a personal computer or more sophisticated computer. The functions of the data-processing unit 4 can be realized by running, on the computer, a dedicated controlling and processing software program previously installed on the same computer. The measured data storage unit 5 and the analysis information storage unit 6 do not need to be constructed using a hardware device built in or connected to the computer. For example, a storage device located on a computer system which is accessible through the Internet or similar network, i.e. a storage device in a cloud-computing system, may also be used for those units.

A characteristic operation in the GC-MS according to the present embodiment is hereinafter described. The following description deals with the case where biological samples (plasma samples) are analyzed to obtain data to be used for a difference analysis aimed at searching for colorectal cancer biomarkers.

<1. Preparation of Biological Samples>
<1.1 Locations where Biological Samples were Collected>

Plasma samples of colorectal cancer patients: National Cancer Center Hospital (Chuo-ku, Tokyo).

Plasma samples of healthy individuals: Center for Public Health Sciences, National Cancer Center (formerly known as Research Center for Cancer Prevention and Screening; Chuo-ku, Tokyo).

<1.2 Conditions of Healthy Individuals>

Qualifying conditions: (1) aged 40 and over, and (2) no detection of abnormality through large intestine endoscopy.

Exclusion criteria: (1) past medical history of one or more of the colorectal polyp, colorectal cancer, and inflammatory bowel disease (IBD); (2) past medical history of an advanced cancer different from colorectal cancer in the last ten years; (3) presence of a familial colorectal cancer patient in relatives; and (4) case of incomplete total colonoscopy.

<1.3 Condition of Colorectal Cancer Patients>

Patients who have already been found to have colorectal cancer at one of stages 0 to 2 through pathological diagnosis or similar tests.

<1.4 Preparation of Plasma Samples for Analysis>

Plasma samples of colorectal cancer patients: EDTA-2Na was added to blood samples collected from the subjects. After being left at room temperature for 15-30 minutes, the samples were refrigerated at 4□. Subsequently, the samples were centrifugally separated (at 3000 rpm for 10 minutes) within 24 hours from the blood sampling, to obtain plasma samples.

Plasma samples of healthy individuals: EDTA-2Na was added to blood samples collected from the subjects. After being left at room temperature for approximately 30 minutes, the samples were refrigerated at 4□. Subsequently, the samples were centrifugally separated (at 3000 rpm for 10 minutes) within 1-6 hours from the blood sampling, to obtain plasma samples.

An optimum quantity of one or more kinds of stable isotope reagents selected from the 22 kinds of reagents listed below was added to each of the plasma samples obtained from the colorectal cancer patients and healthy individuals. Furthermore, a 0.5-mg/mL solution of 2-isopropylmalic acid (2-IPMA) as the internal standard was added to each sample to obtain plasma samples for analysis (which correspond to the biological samples for analysis in the present invention).

Stable isotope reagents: $^{13}C_3$-lactic acid, $^{13}C_2$-oxalic acid, $^2H_3$-sarcosine, $^2H_8$-valine, $^{13}C_3$-dihydroxyacetone, $^2H_{10}$-isoleucine, $^{13}C_4$-fumaric acid, $^{13}C_4$-malic acid, $^2H_3$-aspartic acid, $^{13}C_5$-glutamic acid, $^{13}C_6$-4-hydroxybenzoic acid, $^2H_3$-lauric acid, $^{13}C_5$-ribose, $^{13}C_2$-taurine, $^2H_4$-citric acid, $^2H_7$-ornithine, $^{13}C_6$-tyrosine, $^{13}C_6$-dopa, $^2H_6$-kynurenine, $^2H_8$-cystamine, $^{13}C_{11}$-tryptophan, and $^2H_3$-2-hydroxybutyric acid An optimum quantity of the same stable isotope reagents as the ones added to the plasma samples for analysis was also added to a commercial plasma product (marketed by Kojin Bio Co., Ltd.) to obtain the standard plasma sample for analysis (which corresponds to the standard sample for analysis in the present invention).

<1.5 Pretreatment of Plasma Samples for Analysis and Standard Plasma Sample for Analysis>

The plasma samples for analysis and the standard plasma sample for analysis were subjected to deproteinization by methanol extraction, concentration and drying of supernatant, and oximation by a 20-mg/mL solution of methylhydroxyamine hydrochloride dissolved in pyridine.

<2. Analysis By GC-MS>

Figure 3:
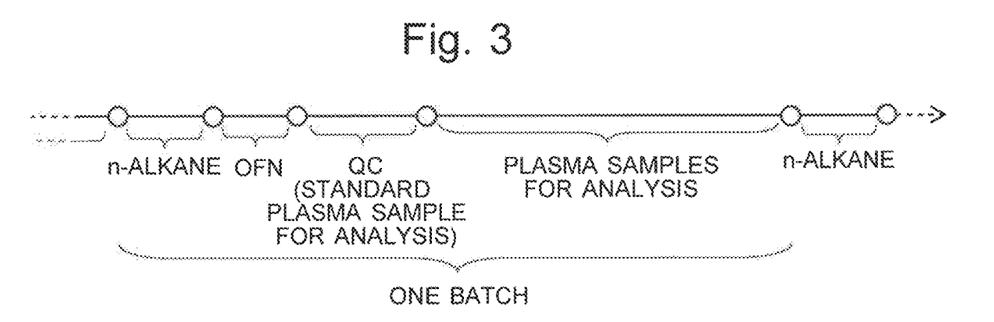
FIG. 3 is a diagram showing one example of the analysis schedule for one batch of analyses.

FIG. 3 shows the analysis schedule. In FIG. 3, "n-Alkane" represents a mixed solution containing 27 kinds of normal alkanes with their carbon numbers ranging from 7 to 33. "OFN" represents a 100-pg/μL solution of octafluoronaphthalene. These solutions correspond to the sample for device evaluation in the present invention. "QC" represents the standard plasma sample for analysis with 22 kinds of stable isotope reagents added. As shown in FIG. 3, the four kinds of samples including n-alkane, OFN, QC and a plurality of plasma samples for analysis were analyzed in series. The cycle of analyses for the four samples was handled as one batch of analyses, and the analyses were repeated for a plurality of batches. The series of analyses for the four kinds of samples were performed according to the method file described in the batch file stored in the batch file storage section 62.

<3 Evaluation Criteria>

Based on mass spectra and mass chromatograms created from the analysis results in each batch of analyses, the evaluation processor 45 evaluated the quality of the data of one set of plasma samples for analysis according to the following evaluation criteria.

<3.1 Exclusion Criteria for Data of Plasma Sample for Analysis>

(1) On a mass spectrum created based on the result of the analysis of each of the one set of plasma samples for analysis, the peak intensity of an ion corresponding to a predetermined internal standard reagent (e.g. 2-isopropylmalic acid), or that of one or more stable isotope reagents (e.g. $^{13}C_6$-4-hydroxybenzoic acid), is outside the range of ±50% of the average of the four middle data in the data of the one set of plasma samples.

(2) The peak of an ion corresponding to the stable isotope reagent added to the plasma sample for analysis is not detected on a mass spectrum created based on the result of the analysis of each of the one set of plasma samples for analysis.

(3) One batch of analyses are stopped halfway.

(4) The peak intensity of the stable isotope reagent determined from a mass chromatogram created based on the result of the analysis of the standard plasma sample for analysis performed before and after the analysis of one set of plasma samples for analysis in one batch of analyses is outside a predetermined range.

(5) The difference in the retention time of n-alkane having the same carbon number, determined from mass chromatograms created based on the result of the analysis of the n-alkane performed before and after the analysis of one set of plasma samples for analysis in one batch of analyses, is equal to or greater than 1.5 seconds.

(6) The intensity of a peak which appears in a mass spectrum at a predetermined retention time, created based on the result of the analysis of the OFN performed before and after the analysis of one set of plasma samples for analysis in one batch of analyses, is outside a predetermined range.

If there is a piece of data which satisfies condition (1) or (2) among the data of one set of plasma samples for analysis, that piece of data of the plasma sample for analysis is excluded from the data to be analyzed. Besides, the data of one set of plasma samples for analysis which satisfies any one of the conditions (3)-(6) are entirely excluded from the data to be analyzed.

Example

Figure 4:
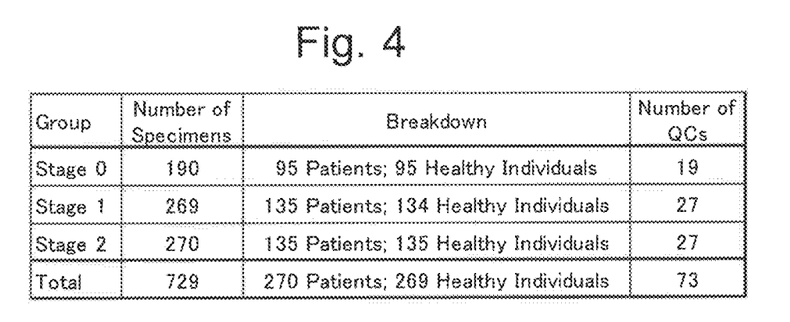
FIG. 4 is a table showing the number and breakdown of the specimens used in an example of the present invention.

A differential analysis between colorectal cancer patients and healthy individuals was performed by evaluating each of the sets of data of plasma samples for analysis obtained by performing the previously described preparation treatment on plasma samples collected from 729 subjects. The result is hereinafter described. As shown in FIG. 4, the 729 subjects were composed of 365 colorectal cancer patients (95 patients at stage 0, 135 patients at stage 1, and 135 patients at stage 2) and 364 healthy individuals. The number of standard plasma samples analyzed along with the plasma samples collected from the 729 subjects (QC number) was 69.

Table 1 shows the batch formation and analysis schedule for the 729 plasma samples for analysis. Although only the plasma samples for analysis (specimens) and standard plasma samples for analysis (QC) are shown in Table 1, the analyses of the samples for device evaluation (n-alkane and OFN) are also included in one batch of analyses. For example, the plasma samples for analysis collected from the 135 colorectal cancer patients at stage 2 were divided into 27 sets along with the plasma samples for analysis collected from 135 healthy individuals, and each of the 27 sets of plasma samples for analysis was analyzed in one batch of analyses along with the samples for device evaluation (n-alkane and OFN) and the standard plasma samples for analysis (QC).

TABLE 1

| Stage II (135 patients, 135 healthy individuals, and 27 QCs) | | |
| --- | --- | --- |
| 1$^{st}$ day | Batches 1-7 | Specimens 1-70, QCs 1-7 |
| 2$^{nd}$ day | Batches 8-11 | Specimens 71-110, QCs 8-11 |
| 3$^{rd}$ day | Batches 12-18 | Specimens 111-180, QCs 12-18 |
| 4$^{th}$ day | Batches 19-25 | Specimens 181-250, QCs 19-25 |
| 5$^{th}$ day | Batches 26-27 | Specimens 251-270, QCs 26-27 |
| Stage I (135 patients, 134 healthy individuals, and 27 QCs) | | |
| 6$^{th}$ day | Batches 1-5 | Specimens 1-50, QCs 1-5 |
| 7$^{th}$ day | Batches 6-9 | Specimens 51-90, QCs 6-9 |
| 8$^{th}$ day | Batches 10-12 | Specimens 91-120, QCs 10-12 |
| 9$^{th}$ day | Batches 13-19 | Specimens 121-190, QCs 13-19 |
| 10$^{th}$ day | Batches 20-27 | Specimens 191-269, QCs 20-27 |
| Stage 0 (95 patients, 95 healthy individuals, and 19 QCs) | | |
| 11$^{th}$ day | Batches 1-7 | Specimens 1-70, QCs 1-7 |
| 12$^{th}$ day | Batches 8-11 | Specimens 71-110, QCs 8-11 |
| 13$^{th}$ day | Batches 12-18 | Specimens 111-180, QCs 12-18 |
| 14$^{th}$ day | Batches 19 | Specimens 181-190, QC 19 |
| Total: 365 patients, 364 healthy individuals, and 73 QCs | | |

Figure 5A:
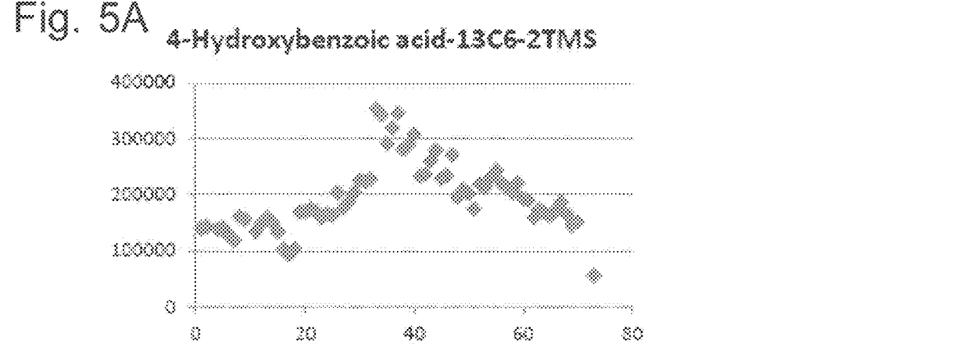
FIG. 5A is a graph showing the peak area ratio of $^{13}C_6$-4-hydroxybenzoic acid as a stable isotope reagent, obtained from a mass chromatogram created based on the result of an analysis of standard plasma samples for analysis.
Figure 5B:
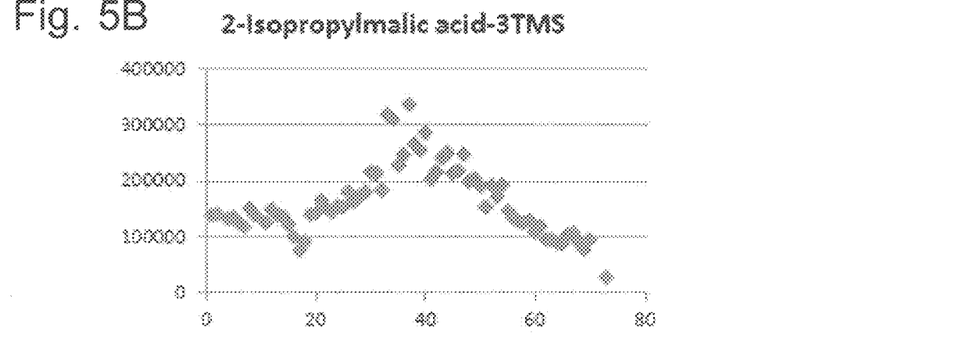
FIG. 5B is a graph showing the peak area ratio of 2-isopropylmalic acid (2-IPMA) as an internal standard, obtained from a mass chromatogram created based on the result of an analysis of standard plasma samples for analysis.
Figure 6A:
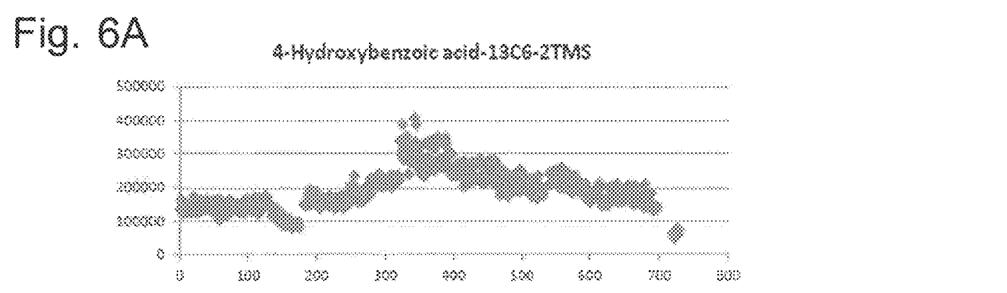
FIG. 6A is a graph showing the peak area ratio of $^{13}C_6$-4-hydroxybenzoic acid as a stable isotope reagent, obtained from a mass chromatogram created based on the result of an analysis of plasma samples for analysis.
Figure 6B:
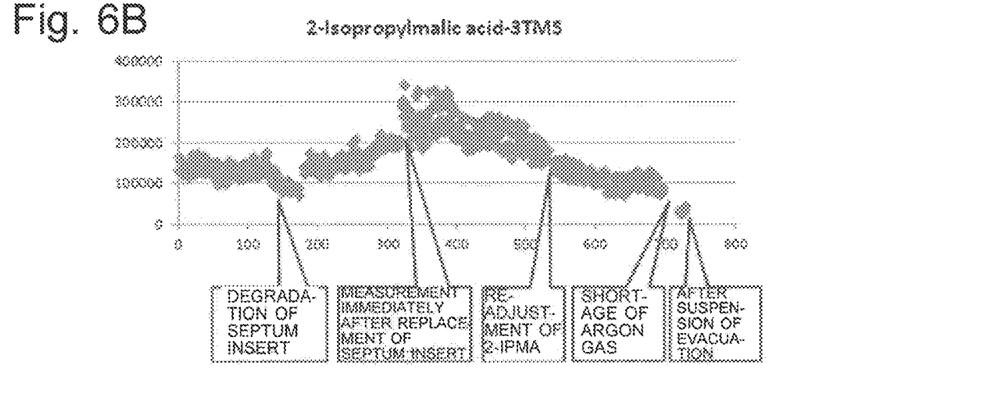
FIG. 6B is a graph showing the peak area ratio of 2-IPMA as an internal standard, obtained from a mass chromatogram created based on the result of an analysis of plasma samples for analysis.

FIGS. 5A and 5B respectively show the peak area ratio of $^{13}C_6$-4-hydroxybenzoic acid as a stable isotope reagent and that of 2-IPMA as the internal standard, obtained from mass chromatograms created based on the results of the analyses of the 73 standard plasma samples for analysis. FIGS. 6A and 6B respectively show the peak area ratio of $^{13}C_6$-4-hydroxybenzoic acid and that of 2-IPMA, obtained from mass chromatograms created based on the results of the analyses of the 729 plasma samples for analysis. In FIGS. 5A, 5B, 6A and 6B, the horizontal axis indicates the numerical values showing the order of measurement of the samples, while the vertical axis indicates the area ratio.

The results shown in FIGS. 5A, 5B, 6A and 6B were the results obtained through a series of analyzing operations during which the following malfunctions (1)-(5) occurred in the GC-MS. The timings at which those malfunctions occurred are indicated in FIG. 6B.

(1) Degradation of the septum insert.
(2) Analysis immediately after the replacement of the septum insert.
(3) Repreparation of 2-IPMA.
(4) Shortage of argon gas.
(5) Analysis after the suspension of the evacuation.

FIGS. 5A, 5B, 6A and 6B demonstrate that any of those malfunctions causes a noticeable change in the detection result (area ratio), and this change similarly occurs in both the detection result of the standard plasma sample for analysis and that of the plasma samples for analysis. The detection becomes totally impossible in the case of malfunction (4).

Figure 7:
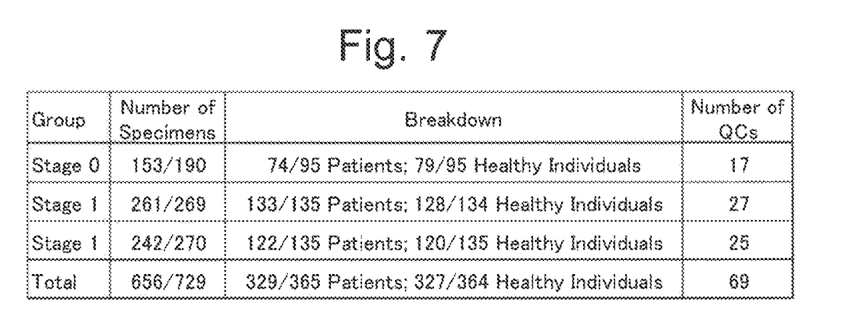
FIG. 7 is a table showing the number and breakdown of the specimens used in an example of the present invention, along with the number and breakdown of the specimens evaluated as being high in quality.

FIG. 7 shows the result of the evaluation of the quality of the plasma samples for analysis based on the results of the batch analyses shown in Table 1 and the aforementioned evaluation criteria. In FIG. 7, the figure on the right side of the slash (/) indicates the number of specimens, while the figure on the left side indicates the number of specimens evaluated as being high in quality. For example, among the 190 specimens of the plasma samples for analysis at stage 0, 153 specimens were evaluated as being high in quality, while 37 specimens were evaluated as being low in quality.

In the present example, only the specimens (plasma samples for analysis) which were evaluated as being high in quality were used for the difference analysis between the colorectal cancer patients and healthy individuals. The amounts of 64 components contained in the plasma samples for analysis were used for the difference analysis. FIGS. 8A and 8B show an example of the data for one batch of analyses. The suffix "(SI ratio)" attached to the component name in FIGS. 8A and 8B indicates that the corresponding numerical values were corrected using the stable isotope reagent having the same structure as that component and contained in the specimens. The numerical values corresponding to the other components were corrected using the internal standard. A stable isotope reagent added to a biological sample to evaluate this biological sample is a stable isotopically labeled in vivo metabolite contained in the biological sample, and its content is previously known. Therefore, a detection value of this stable isotope reagent can be used to correct the detection value of a component having the same structure as the stable isotope reagent.

The present invention is not limited to the previously described embodiment and example. It is possible to make appropriate changes or modifications within the spirit of the present invention.

For example, in the previous embodiment, all of the 22 kinds of stable isotope reagents are added to the original biological samples (plasma samples) to obtain biological samples for analysis. However, the addition of only one of the 22 kinds of stable isotope reagents may be sufficient. A reagent different from the aforementioned stable isotope reagents may also be added. The stable isotope reagents are not limited to the 22 kinds used in the previous embodiment and example. Any in vivo metabolite that is appropriate for the kind of biological sample to be analyzed (i.e. an in vivo metabolite contained in the biological sample concerned, or a substance having similar properties to the in vivo metabolite) may be isotopically labeled and used as a stable isotope reagent. The number of stable isotope reagents added to each biological sample only need to be at least equal to the number of in vivo metabolites to be analyzed. In this case, if two kinds of in vivo metabolites contained in biological samples need to be analyzed, either those two kinds of in vivo metabolites or two kinds of substances having similar properties to those two kinds of in vivo metabolites should be isotopically labeled and added as stable isotope reagents to the original biological samples to obtain biological samples for analysis.

Even when there are three kinds of in vivo metabolites to be analyzed, the addition of a single stable isotope reagent to the biological sample may be sufficient to obtain the biological sample for analysis, if those three kinds of in vivo metabolites have similar properties.

REFERENCE SIGNS LIST

1 . . . GC Unit
12 . . . Column
2 . . . MS Unit
20 . . . Ion Source
21 . . . Quadrupole Mass Filter
22 . . . Ion Detector
3 . . . Analogue-to-Digital Converter
4 . . . Data-Processing Unit
41 . . . Data Collector
42 . . . Component Extractor 43 . . . Component Storage Section
44 . . . Graph Creator
45 . . . Evaluation Processor
46 . . . Result Display Processor
5 . . . Measured Data Storage Unit
6 . . . Analysis Information Storage Unit
61 . . . Method File Storage Section
62 . . . Batch File Storage Section
63 . . . Evaluation Information Storage Section
64 . . . Analysis Result Database
65 . . . Evaluation Result Database
7 . . . Input Unit
8 . . . Display Unit

The invention claimed is:

1. A method for chromatographic mass spectrometry including steps of temporally separating components in a sample by a chromatograph selected from the group consisting of a gas chromatography and a liquid chromatography, and subsequently separating and detecting ions originating from the components according to mass-to-charge ratios of the ions by a mass analyzer, the method comprising:
 a) a first preparation process in which a plurality of biological samples for analysis are prepared by adding, to each of a plurality of original biological samples, at least one stable isotope reagent obtained by stable isotopically labeling a predetermined in vivo metabolite contained in the original biological samples, and then performing a pretreatment for chromatographic mass spectrometry on the original biological samples, the pretreatment for chromatographic mass spectrometry being selected from the group consisting of deproteinization and oximation;
 b) a second preparation process in which a standard sample for analysis is prepared by adding, to an original standard sample, the same stable isotope reagent as the one added to the biological samples for analysis, and then performing, on the original standard sample, the same pretreatment as the one performed on the original biological samples;
 c) a first analyzing process in which the plurality of biological samples for analysis are collectively analyzed as one set;
 d) a second analyzing process in which the standard sample for analysis is analyzed before and after the first analyzing process;
 e) a first evaluation process in which: a peak intensity corresponding to the stable isotope reagent contained in each of the biological samples for analysis is determined from each of the mass spectra created based on data obtained in each of the first analyzing process; a median or average of the peak intensity corresponding to the at least one stable isotope reagent contained in the plurality of biological samples for analysis is calculated; and a quality of each of the original biological samples and the first preparation process are evaluated based on whether or not the peak intensity corresponding to the stable isotope reagent contained in each of the biological samples for analysis is within a predetermined range centering on the median or average; and
 f) a second evaluation process in which a quality of the pretreatment and/or a quality of the analysis is evaluated by mass spectra created based on the data obtained in the second analyzing process.

2. A method for chromatographic mass spectrometry including steps of temporally separating components in a sample by a chromatograph selected from the group consisting of a gas chromatography and a liquid chromatography, and subsequently separating and detecting ions originating from the components according to mass-to-charge ratios of the ions by a mass analyzer, the method comprising:
 a) a first preparation process in which a plurality of biological samples for analysis are prepared by adding, to each of a plurality of original biological samples, at least one stable isotope reagent obtained by stable isotopically labeling a predetermined in vivo metabolite contained in the original biological samples, and then performing a pretreatment for chromatographic mass spectrometry on the original biological samples, the pretreatment for chromatographic mass spectrometry being selected from the group consisting of deproteinization and oximation;
 b) a second preparation process in which a standard sample for analysis is prepared by adding, to an original standard sample, the same stable isotope reagent as the one added to the biological samples for analysis, and then performing, on the original standard sample, the same pretreatment as the one performed on the original biological samples;
 c) a first analyzing process in which the plurality of biological samples for analysis are collectively analyzed as one set;
 d) a second analyzing process in which the standard sample for analysis is analyzed before and after the first analyzing process;
 e) a first evaluation process in which a quality of each of the original biological samples is evaluated based on whether or not a peak of an ion corresponding to the stable isotope reagent contained in each of the biological samples for analysis is present on a mass spectrum created based on data obtained in each of the first analyzing process; and
 f) a second evaluation process in which a quality of the pretreatment and/or a quality of the analysis is evaluated by mass spectra created based on the data obtained in the second analyzing process.

3. The method for chromatographic mass spectrometry according to claim 1, wherein:
 an internal standard reagent which is not contained in a living organism is added to each of the original biological samples in the first preparation process; and
 the first preparation process is performed as follows: a peak intensity corresponding to either the internal standard reagent or the stable isotope reagent contained in each of the biological samples for analysis is determined from each of the mass spectra created based on data obtained in each of the first analyzing process; a median or average of the peak intensity corresponding to either the internal standard reagent or the at least one stable isotope reagent contained in the plurality of biological samples for analysis is calculated; and the quality of each of the original biological samples and the first preparation process are evaluated based on whether or not the peak intensity corresponding to either the internal standard reagent or the stable isotope reagent contained in each of the biological samples for analysis is within a predetermined range centering on the median or average.

4. The method for chromatographic mass spectrometry according to claim 2, wherein:
 an internal standard reagent which is not contained in a living organism is added to each of the original biological samples in the first preparation process; and
 the first evaluation process is performed as follows: the quality of each of the original biological samples is evaluated based on whether or not a peak of an ion corresponding to either the internal standard reagent or the stable isotope reagent contained in each of the biological samples for analysis is present on a mass spectrum created based on data obtained in each of the first analyzing process.

5. The method for chromatographic mass spectrometry according to claim 1, wherein:
the stable isotope reagent is at least one substance selected from $^{13}C_3$-lactic acid, $^{13}C_2$-oxalic acid, $^2H_3$-sarcosine, $^2H_8$-valine, $^{13}C_3$-dihydroxyacetone, $^2H_{10}$-isoleucine, $^{13}C_4$-fumaric acid, $^{13}C_4$-malic acid, $^2H_3$-aspartic acid, $^{13}C_5$-glutamic acid, $^{13}C_6$-4-hydroxybenzoic acid, $^2H_3$-lauric acid, $^{13}C_5$-ribose, $^{13}C_2$-taurine, $^2H_4$-citric acid, $^2H_7$-ornithine, $^{13}C_6$-tyrosine, $^{13}C_6$-dopa, $^2H_6$-kynurenine, $^2H_8$-cystamine, $^{13}C_{11}$-tryptophan, and $^2H_3$-2-hydroxybutyric acid.

6. The method for chromatographic mass spectrometry according to claim 2, wherein:
the stable isotope reagent is at least one substance selected from $^{13}C_3$-lactic acid, $^{13}C_2$-oxalic acid, $^2H_3$-sarcosine, $^2H_8$-valine, $^{13}C_3$-dihydroxyacetone, $^2H_{10}$-isoleucine, $^{13}C_4$-fumaric acid, $^{13}C_4$-malic acid, $^2H_3$-aspartic acid, $^{13}C_5$-glutamic acid, $^{13}C_6$-4-hydroxybenzoic acid, $^2H_3$-lauric acid, $^{13}C_5$-ribose, $^{13}C_2$-taurine, $^2H_4$-citric acid, $^2H_7$-ornithine, $^{13}C_6$-tyrosine, $^{13}C_6$-dopa, $^2H_6$-kynurenine, $^2H_8$-cystamine, $^{13}C_{11}$-tryptophan, and $^2H_3$-2-hydroxybutyric acid.

7. The method for chromatographic mass spectrometry according to claim 1, further comprising:
a third analyzing process in which a sample for device evaluation is analyzed before and after the first analyzing process; and
a third evaluation process in which an abnormality in a chromatograph or a mass analyzer used for the analysis is evaluated by a mass chromatogram or a mass spectrum created based on data obtained in the third analyzing process.

8. The method for chromatographic mass spectrometry according to claim 2, further comprising:
a third analyzing process in which a sample for device evaluation is analyzed before and after the first analyzing process; and
a third evaluation process in which an abnormality in a chromatograph or a mass analyzer used for the analysis is evaluated by a mass chromatogram or a mass spectrum created based on data obtained in the third analyzing process.

9. The method for chromatographic mass spectrometry according to claim 7, wherein:
the sample for device evaluation contains an octafluoronaphthalene solution; and
an abnormality in the mass analyzer is evaluated in the third evaluation process by comparing mass chromatograms at a mass-to-charge ratio corresponding to the octafluoronaphthalene created based on the data obtained by analyzing the sample for device evaluation before and after the first analyzing process.

10. The method for chromatographic mass spectrometry according to claim 8, wherein:
the sample for device evaluation contains an octafluoronaphthalene solution; and
an abnormality in the mass analyzer is evaluated in the third evaluation process by comparing mass chromatograms at a mass-to-charge ratio corresponding to the octafluoronaphthalene created based on the data obtained by analyzing the sample for device evaluation before and after the first analyzing process.

11. The method for chromatographic mass spectrometry according to claim 1, wherein:
the biological samples for analysis and the standard sample for analysis contain $^{13}C_6$-4-hydroxybenzoic acid as the stable isotope reagent.

12. The method for chromatographic mass spectrometry according to claim 2, wherein:
the biological samples for analysis and the standard sample for analysis contain $^{13}C_6$-4-hydroxybenzoic acid as the stable isotope reagent.

* * * * *